(12) United States Patent
Lackey et al.

(10) Patent No.: US 7,338,966 B2
(45) Date of Patent: Mar. 4, 2008

(54) SUBSTITUTED OXINDOLE DERIVATIVES AS TYROSINE KINASE INHIBITORS

(75) Inventors: Karen Elizabeth Lackey, Durham, NC (US); Edgar Raymond Wood, III, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 427 days.

(21) Appl. No.: 11/148,635

(22) Filed: Jun. 9, 2005

(65) Prior Publication Data

US 2005/0228025 A1    Oct. 13, 2005

Related U.S. Application Data

(63) Continuation of application No. 10/362,743, filed on Feb. 27, 2003, now Pat. No. 7,071,217.

(51) Int. Cl.
*A61K 31/44* (2006.01)
*C07D 401/12* (2006.01)

(52) U.S. Cl. ............ 514/339; 546/277.7; 548/138; 548/483; 548/484; 548/472; 514/363; 514/418

(58) Field of Classification Search ............ 549/277.7; 548/138, 483, 484, 472; 514/339, 418, 363
See application file for complete search history.

(56) References Cited

U.S. PATENT DOCUMENTS

| | | | |
|---|---|---|---|
| 6,350,747 B1 | 2/2002 | Glennon et al. | |
| 6,369,086 B1 | 4/2002 | Davis et al. | |
| 6,387,919 B1 | 5/2002 | Davis et al. | |
| 6,492,398 B1 | 12/2002 | Vyas | |
| 6,498,176 B1 | 12/2002 | Lackey et al. | |
| 6,541,503 B2 | 4/2003 | Davis et al. | |
| 6,620,818 B1 | 9/2003 | Davis | |
| 6,624,171 B1 | 9/2003 | Harris et al. | |
| 6,818,632 B2 * | 11/2004 | Glennon et al. | 514/81 |
| 7,071,217 B2 * | 7/2006 | Dickerson et al. | 514/339 |

FOREIGN PATENT DOCUMENTS

| | | |
|---|---|---|
| DE | 198 24 922 | 12/1999 |
| WO | 99/15500 | 4/1999 |
| WO | 00/56710 | 9/2000 |
| WO | 03/027111 | 4/2003 |

OTHER PUBLICATIONS

Kamel, Mohamed, et al., "Monoazo metal complex forming dyes. V. Dyes derived from isatin," Chemical Abstracts, vol. 67, No. 8, abstract No. 33812 (Aug. 12, 1967).

* cited by examiner

*Primary Examiner*—Golam M. M. Shameem
(74) *Attorney, Agent, or Firm*—John L. Lemanowicz

(57) ABSTRACT

The present invention is related to oxindole derivatives of structure (I), compositions containing the same, and methods of use and manufacture of the same. Such compounds generally are useful pharmacologically as agents in those disease states alleviated by the alteration of mitogen activated signaling pathways in general, and in particular in the inhibition or antagonism of protein kinases, which pathologically involve aberrant cellular proliferation. Such disease states include tumor growth, restenosis, atherosclerosis, pain and thrombosis. In particular, the present invention relates to a series of substituted oxindole compounds, which exhibit Trk family protein tyrosine kinase inhibition, and which are useful in cancer therapy and chronic pain indications.

8 Claims, No Drawings

SUBSTITUTED OXINDOLE DERIVATIVES AS TYROSINE KINASE INHIBITORS

This application is a continuation of Ser. No. 10/362,743, filed Feb. 27, 2003, now U.S. Pat. No. 7,071,217 which claims priority to Ser. No. 60/230,050, filed Sep. 1, 2000. Both applications are incorporated herein by reference in their entirety.

BACKGROUND OF THE INVENTION

The present invention is related to oxindole derivatives, compositions containing the same, and methods of use and manufacture of the same. Such compounds generally are useful pharmacologically as agents in those disease states alleviated by the alteration of mitogen activated signaling pathways in general, and in particular in the inhibition or antagonism of protein kinases, which pathologically involve aberrant cellular proliferation. Such disease states include tumor growth, restenosis, atherosclerosis, pain and thrombosis. In particular, the present invention relates to a series of substituted oxindole compounds, which exhibit Trk family protein tyrosine kinase inhibition, and which are useful in cancer therapy and chronic pain indications.

Cell growth, differentiation, metabolism and function are very tightly controlled in higher eukaryotes. The ability of a cell to rapidly and appropriately respond to the array of external and internal signals it continually receives is of critical importance in maintaining a balance between these processes (Rozengurt, Current Opinion in Cell Biology 1992, 4, 161-5; Wilks, Progress in Growth Factor Research 1990, 2, 97-111). The loss of control over cellular regulation can often lead to aberrant cell function or death, often resulting in a disease state in the parent organism.

The protein kinases represent a large family of proteins which play a central role in the regulation of a wide variety of cellular processes and maintaining control over cellular function (Hanks, et al., Science 1988, 241, 42-52). A partial list of such kinases includes ab1, ATK, bcr-ab1, Blk, Brk, Btk, c-kit, c-met, c-src, CDK1, CDK2, CDK4, CDK6, cRaf1, CSF1R, CSK, EGFR, ErbB2, ErbB3, ErbB4, ERK, Fak, fes, FGFR1, FGFR2, FGFR3, FGFR4, FGFR5, Fgr, FLK-4, fit-1, Fps, Frk, Fyn, Hck, IGF-1R, INS-R, Jak, KDR, Lck, Lyn, MEK, p38, PDGFR, PIK, PKC, PYK2, ros, tie$_1$, tie$_2$, TRK, Yes, and Zap70.

One of the most commonly studied pathways involving kinase regulation is cellular signalling from receptors at the cell surface to the nucleus (Crews and Erikson, Cell 1993, 74, 215-7). One example of this pathway includes a cascade of kinases in which members of the growth factor receptor tyrosine kinases (such as EGF-R, PDGF-R, VEGF-R, IGF1-R, the Insulin receptor), deliver signals through phosphorylation to other kinases such as Src tyrosine kinase, and the Raf, Mek and Erk serine/threonine kinase families (Crews and Erikson, Cell 1993, 74, 215-7; Ihle, et al., Trends in Biochemical Sciences 1994, 19, 222-7). Each of these kinases is represented by several family members (Pelech and Sanghera, Trends in Biochemical Sciences 1992, 17, 233-8) which play related, but functionally distinct roles. The loss of regulation of the growth factor signaling pathway is a frequent occurrence in cancer as well as other disease states.

A variety of evidence suggests that nerve growth factor (NGF) may be a mediator of some persistent pain states, including neuropathic and inflammatory pain. For example: a) NGF is rapidly elevated in inflamed tissues.; b) NGF specific antibodies substantially diminish inflammatory hypersensitivity; c) injection of NGF into adult rats causes a profound hypersensitivity to noxious heat and mechanical stimuli; and d) low level administration of recombinant NGF induces hyperalgesia in healthy humans. NGF produces hyperalgesia through several potential mechanisms. NGF results in the upregulation of peptide neurotransmitters in neurons that detect painful stimuli (nociceptors). NGF increases the excitability of spinal cord neurons to activation. Mast cells express NGF receptors and NGF triggers the release of granules containing histamine and serotonin. Histamine and serotonin are capable of sensitizing nociceptors. (Wood, John (2000) Pathology of Visceral Pain: Molecular Mechanisms and Therapeutic Implications II. Genetic Aproaches to Pain Therapy. *Am. J. Physiol.* 278(40), G507-G512.)

NGF binds to two different receptors, the neurotrophin receptor p75 (p75NTR) and TrkA. p75NTR is a member of a family of receptors that includes tumor necrosis factor receptor (TNFR) and FAS/AP01. These receptors have in common a cysteine-rich motif in the extracellular domain, a single transmembrane domain, and a cytoplasmic domain. p75NTR signals in a fashion similar to TNFR and FAS via the activation of NFkB, JNK, and ceramide production. The functional significance of p75NTR in NGF mediated biological responses is not clear. Proposed functions include a) modulation of TrkA driven responses and b) induction of cell death in cells that express p75NTR, but not TrkA.

TrkA appears to be the primary mediator of NGF driven biological responses. The most compelling evidence for this comes from NGF and TrkA knockout mice. Mice defective in either the ligand or receptor component of this system have remarkably similar phenotypes. Examples of these phenotypes include severe sensory defects characterized by a complete loss of nociceptive activity and deficiencies in thermoception. Anatomically these mice exhibit extensive peripheral nervous system cell loss in trigeminal, dorsal root, and sympathetic ganglia. Other evidence for the involvement of TrkA in NGF driven responses comes from the study of the PC12 cell line. PC12 cells express high levels of p75NTR and TrkA. NGF causes PC12 cells to differentiate into a neuronal phenotype characterized by the development of axonal projections. Loss of TrkA prevents PC12 cells from differentiating in response to NGF. (Eggert, A.; Ikegaki, N.; Lui, X.; Chou, T.; Lee, V.; Trojanowski, J. Q.; Brodeur, G. M.; (2000) Molecular Dissection of TrkA Signal Transduction Pathways Mediating Differentiation in human Neuroblastoma Cells. *Oncogene*, 19(16), 2043-2051.)

There is evidence that Trk tyrosine kinases play a role in the development of a variety of cancers including, for example, breast and prostate cancer. (Guate, J. L. et al, (1999) Expression of p75LNGFR and Trk Neurotrophin Receptors in Normal and Neoplastic Human Prostate, *BJU Int*. 84(4), 495-502; Tagliabue, E. et al, S. Nerve Growth Factor cooperates with p185HER2 in Activating Growth of Human Breast Carcinoma Cells, (2000) *J. Biol. Chem*. 275(8), 5388-5394). Further, there is strong evidence that mediation of the Trk kinase signaling will provide beneficial biological effects. (LeSauteur, L. et al, (1998) Development and Uses of Small Molecule Ligands of TrkA Receptors, *Adv. Behav. Biol*. 49, 615-625; Zhu, Z. et al, (1999) Nerve Growth Factor Expression Correlates with Perineural Invasion and Pain in Human Pancreatic Cancer, *Journal of Clinical Oncology*, 17(8), 2419-28; Friess, H et al, Nerve Growth Factor and its High-Affinity Receptor in Chronic Pancreatitis, (1999) *Annals of Surgery* 230(5), 615-24.)

TrkA is a receptor tyrosine kinase that belongs to a subfamily of tyrosine kinases that includes TrkB, and TrkC TrkB and TrkC are structurally similar to TrkA, but respond to different ligands in the neurotrophin family. NGF signaling through TrkA has been best characterized in the PC12 system and is similar to signal transduction mechanisms of other tyrosine kinase receptors. NGF exists as a homodimer. Binding of NGF promotes dimerization, and autophoshphorylation of TrkA. Phosphorylation of TrkA increases the catalytic activity of the kinase domain and creates binding sites for SH2 domain containing cytoplasmic proteins. SH2 domain binding events initiate the activation of several signal transduction pathways such as PLCg, ras, P13 kinase/AKT, and Raf/MEK/ERK. (Frade, J. M. et al (1998) Nerve growth factor: two receptors, multiple functions, *BioEssays* 20: 137-145; Kaplan, D. R. et al, (1997) Signal Transduction by the Neurotrophin Receptors, *Current Opinion in Cell Biology*. 9: 213-221; Barbacid, M. (1995) Neurotrophic factors and their receptors, *Current Opinion in Cell Biology*. 7:148-155; Snider, W. D. (1994) Functions of the Neurotrophins During Nervous System Development: What the Knockouts are Teaching Us, *Cell*, 77:627-638.)

The selective inhibition of Trk family of kinases (TrkA, TrkB, and TrkC) is therefore an object of the present invention.

There is a continuing need in the medical field for new and more effective treatments for cancer and for the relief of pain, especially chronic pain. Because TrkA and other Trk kinases may serve as a mediator of NGF driven biological responses, inhibitors of TrkA and other Trk kinases may provide an effective treatment for cancer and for chronic pain states. At present, there is an unmet need for small molecule compounds that may be readily synthesized and are potent inhibitors of TrkA and other Trk family kinases. The present inventors have now discovered novel oxindole derivative compounds that selectively inhibit the catalytic activity of TrkA and/or other Trk family kinases thereby providing new treatment strategies for those afflicted with cancer and chronic pain.

It is additionally possible that inhibitors of certain kinases may have utility in the treatment of diseases when the kinase is not mis-regulated, but is nonetheless essential for maintenance of the disease state.

SUMMARY OF THE INVENTION

In one aspect the present invention provides, compounds of the formula (I):

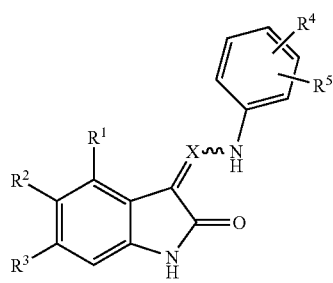

wherein

X is N, CH, CCF$_3$, or C(C$_{1-12}$ aliphatic);

R$^1$ is hydrogen, C$_{1-12}$ aliphatic, thiol, hydroxy, hydroxy-C$_{1-12}$ aliphatic, Aryl, Aryl-C$_{1-12}$ aliphatic, R$^6$-Aryl-C$_{1-12}$ aliphatic, Cyc, Cyc-C$_{1-6}$ aliphatic, Het, Het-C$_{1-12}$ aliphatic, C$_{1-12}$ alkoxy, Aryloxy, amino, C$_{1-12}$ aliphatic amino, di-C$_{1-12}$ aliphatic amino, di-C$_{1-12}$ aliphatic aminocarbonyl, di-C$_{1-12}$ aliphatic aminosulfonyl, C$_{1-12}$ alkoxycarbonyl, halogen, cyano, sulfonamide, or nitro, where R$^6$, Aryl, Cyc and Het are as defined below;

R$^2$ is hydrogen, C$_{1-12}$ aliphatic, N-hydroxyimino-C$_{1-12}$ aliphatic, C$_{1-12}$ alkoxy, hydroxy-C$_{1-12}$ aliphatic, C$_{1-12}$ alkoxycarbonyl, carboxyl C$_{1-12}$ aliphatic, Aryl, R$^6$-Aryl-oxycarbonyl, R$^6$-oxycarbonyl-Aryl, Het, aminocarbonyl, C$_{1-12}$ aliphatic-aminocarbonyl, Aryl-C$_{1-12}$ aliphatic-aminocarbonyl, R$^6$-Aryl-C$_{1-12}$ aliphatic-aminocarbonyl, Het-C$_{1-12}$ aliphatic-aminocarbonyl, hydroxy-C$_{1-12}$ aliphatic-aminocarbonyl, C$_{1-12}$-alkoxy-C$_{1-12}$ aliphatic-aminocarbonyl, C$_{1-12}$ alkoxy-C$_{1-12}$ aliphatic-amino, di-C$_{1-12}$ aliphatic amino, di-C$_{1-12}$ aliphatic aminocarbonyl, di-C$_{1-12}$ aliphatic aminosulfonyl, halogen, hydroxy, nitro, C$_{1-12}$ aliphatic-sulfonyl, aminosulfonyl, or C$_{1-12}$ aliphatic-aminosulfonyl, where Aryl and Het are as defined below; further wherein R$^1$ and R$^2$ are optionally joined to form a fused ring, said fused ring selected from the group as defined for Het below, or any of said fused rings optionally substituted by C$_{1-12}$ aliphatic, halogen, nitro, cyano, C$_{1-12}$ alkoxy, carbonyl-C$_{1-12}$ alkoxy or oxo;

R$^3$ is hydrogen, C$_{1-12}$ aliphatic, hydroxy, hydroxy C$_{1-12}$ aliphatic, di-C$_{1-12}$ aliphatic amino, di-C$_{1-12}$ aliphatic aminocarbonyl, di-C$_{1-12}$ aliphatic aminosulfonyl, C$_{1-12}$ alkoxy, Aryl, Aryloxy, hydroxy-Aryl, Het, hydroxy-Het, Het-oxy, or halogen, where Aryl and Het are as defined below;

further wherein R$^2$ and R$^3$ are optionally joined to form a fused ring, said fused ring selected from the group as defined for Het below, or any of said fused rings optionally substituted by C$_{1-6}$ aliphatic or C$_{1-6}$ aliphatic-carbonyl;

R$^4$ is sulfonic acid, C$_{1-12}$ aliphatic-sulfonyl, sulfonyl-C$_{1-12}$ aliphatic, C$_{1-12}$ aliphatic-sulfonyl-C$_{1-6}$ aliphatic, C$_{1-6}$ aliphatic-amino, R$^7$-sulfonyl, R$^7$-sulfonyl-C$_{1-12}$ aliphatic, R$^7$-aminosulfonyl, R$^7$-aminosulfonyl-C$_{1-12}$ aliphatic, R$^7$-sulfonylamino, aminosulfonyl-C$_1$-C$_{12}$-aliphatic, R$^7$-sulfonylamino-C$_{1-12}$ aliphatic, aminosulfonylamino, di-C$_{1-12}$ aliphatic amino, di-C$_{1-12}$ aliphatic aminocarbonyl, di-C$_{1-12}$ aliphatic aminosulfonyl, di-C$_{1-12}$ aliphatic amino, di-C$_{1-12}$ aliphatic aminocarbonyl, di-C$_{1-12}$ aliphatic aminosulfonyl-C$_{1-12}$ aliphatic, (R$^8$)$_{1-3}$-Arylamino, (R$^8$)$_{1-3}$-Arylsulfonyl, (R$^8$)$_{1-3}$-Aryl-aminosulfonyl, (R$^8$)$_{1-3}$-Aryl-sulfonylamino, Het-amino, Het-sulfonyl, Het-aminosulfonyl, aminoiminoamino, or aminoiminoaminosulfonyl, where R$^7$, R$^8$, Aryl and Het are as defined below;

R$^5$ is hydrogen;

and further wherein R$^4$ and R$^5$ are optionally joined to form a fused ring, said ring selected from the group as defined for Het below, or any of said used rings optionally substituted by C$_{1-12}$ aliphatic, oxo or dioxo;

R$^6$ is C$_{1-12}$ aliphatic, hydroxy, C$_{1-12}$ alkoxy, or halogen;

R$^7$ is hydrogen, C$_{1-12}$ aliphatic, C$_{1-12}$ alkoxy, hydroxy-C$_{1-12}$ alkoxy, hydroxy-C$_{1-12}$ aliphatic, carboxylic acid, C$_{1-12}$ aliphatic-carbonyl, Het, Het-C$_{1-12}$-aliphatic, Het-C$_{1-12}$-alkoxy, di-Het-C$_{1-12}$-alkoxy Aryl, Aryl-C$_{1-12}$-aliphatic, Aryl-C$_{1-12}$-alkoxy, Aryl-carbonyl, C$_{1-18}$ alkoxyalkoxyalkoxyalkoxyaliphatic, or hydroxyl where Het and Aryl are as defined below;

R$^8$ is hydrogen, nitro, cyano, C$_{1-12}$ alkoxy, halo, carbonyl-C$_{1-12}$ alkoxy or halo-C$_{1-12}$ aliphatic;

Aryl is phenyl, naphthyl, phenanthryl or anthracenyl;

Cyc is cyclopropyl, cyclobutyl, cyclopentyl, cyclohexyl, cycloheptyl or cyclooctyl, any one of which may have one or more degrees of unsaturation;

Het is a saturated or unsaturated heteroatom ring system selected from the group consisting of benzimidazole, dihydrothiophene, dioxin, dioxane, dioxolane, dithiane, dithiazine, dithiazole, dithiolane, furan, imidazole, isoquinoline, morpholine, oxazole, oxadiazole, oxathiazole, oxathiazolidine, oxazine, oxadiazine, piperazine, piperadine, pyran, pyrazine, pyrazole, pyridine, pyrimidine, pyrrole, pyrrolidine, quinoline, tetrahydrofuran, tetrazine, thidiazine, thiadiazole, thiatriazole, thiazine, thiazole, thiomorpholine, thiophene, thiopyran, triazine and triazole, with the proviso that when $R^2$ is thiadiazine, then $R^4$ cannot be methylsulfone;

and the pharmaceutically acceptable salts, solvates, or physiologically functional derivatives thereof including biohydrolyzable esters, biohydrolyzable amides, biohydrolyzable carbamates solvates, hydrates, affinity reagents or prodrugs thereof in either crystalline or amorphous form.

In another aspect of the present invention, there is provided compounds of formula (I):

wherein

X is N, CH, or C($C_{1-6}$ aliphatic);

$R^1$ is hydrogen, $C_{1-6}$ aliphatic, hydroxy-$C_{1-6}$ aliphatic, Aryl-$C_{1-6}$ aliphatic, $R^6$-Aryl-$C_{1-6}$ aliphatic, Cyc-$C_{1-6}$ aliphatic, Het-$C_{1-6}$ aliphatic, $C_{1-6}$alkoxy, Aryloxy, aminocarbonyl, di-$C_{1-6}$ aliphatic amino, di-$C_{1-6}$ aliphatic aminocarbonyl, di-$C_{1-6}$ aliphatic aminosulfonyl, $C_{1-6}$ alkoxycarbonyl, halogen, or nitro, where $R^6$, Aryl, Cyc and Het are as defined below;

$R^2$ is hydrogen, $C_{1-6}$ aliphatic, $R^7$—$C_{1-6}$ aliphatic, $C_{1-6}$alkoxy, hydroxy-$C_{1-6}$ aliphatic, $C_{1-6}$ alkoxycarbonyl, carboxyl $C_{1-6}$ aliphatic, Aryl, $R^6$-Aryl-oxycarbonyl, $R^6$-oxycarbonyl-Aryl, Het, aminocarbonyl, $C_{1-6}$ aliphatic-aminocarbonyl, Aryl-$C_{1-6}$ aliphatic-aminocarbonyl, $R_6$-Aryl-$C_{1-6}$ aliphatic-aminocarbonyl, Het-$C_{1-6}$ aliphatic-aminocarbonyl, hydroxy-$C_{1-6}$ aliphatic-aminocarbonyl, $C_{1-6}$-alkoxy-$C_{1-6}$ aliphatic-aminocarbonyl, $C_{1-6}$ alkoxy-$C_{1-6}$ aliphatic-amino, di-$C_{1-6}$ aliphatic amino, di-$C_{1-6}$ aliphatic aminocarbonyl, di-$C_{1-6}$ aliphatic aminosulfonyl, halogen, hydroxy, nitro, sulfo, $C_{1-6}$ aliphatic-sulfonyl, aminosulfonyl, $C_{1-6}$ aliphatic-aminosulfonyl, or quaternary ammonium, where $R^7$, Aryl and Het are as defined below;

further wherein $R^1$ and $R^2$ are optionally joined to form a fused ring, said fused ring selected from the group as defined for Het above, or any of said fused rings optionally substituted by halogen or oxo;

$R^3$ is hydrogen, $C_{1-6}$ aliphatic, hydroxy, hydroxy $C_{1-6}$ aliphatic, di-$C_{1-6}$ aliphatic amino, di-$C_{1-6}$ aliphatic aminocarbonyl, di-$C_{1-6}$ aliphatic aminosulfonyl, $C_{1-6}$ alkoxy, Aryl, Aryloxy, hydroxy-Aryl, Het, hydroxy-Het, Het-oxy, or halogen, where Aryl and Het are as defined below;

further wherein $R^2$ and $R^3$ are optionally joined to form a fused ring, said fused ring selected from the group as defined for Het above, or any of said fused rings optionally substituted by $C_{1-6}$ aliphatic or $C_{1-6}$ aliphatic-carbonyl;

$R^4$ is sulfonic acid, $C_{1-12}$ aliphatic-sulfonyl, sulfonyl-$C_{1-12}$ aliphatic, $C_{1-12}$ aliphatic-sulfonyl-$C_{1-6}$ aliphatic, $C_{1-6}$ aliphatic-amino, $R^7$-sulfonyl, $R^7$-sulfonyl-$C_{1-12}$ aliphatic, $R^7$-aminosulfonyl, $R^7$-aminosulfonyl-$C_{1-12}$ aliphatic, $R^7$-sulfonylamino, $R^7$-sulfonylamino-$C_{1-12}$ aliphatic, aminosulfonylamino, aminosulfonyl-$C_1$-$C_{12}$-aliphatic, di-$C_{1-12}$ aliphatic amino, di-$C_{1-12}$ aliphatic aminocarbonyl, di-$C_{1-12}$ aliphatic aminosulfonyl, di-$C_{1-12}$ aliphatic amino, di-$C_{1-12}$ aliphatic aminocarbonyl, di-$C_{1-12}$ aliphatic aminosulfonyl-$C_{1-12}$ aliphatic aminosulfonyl-$C_{1-12}$ aliphatic, $(R^8)_{1-3}$-Arylamino, $(R^8)_{1-3}$-Arylsulfonyl, $(R^8)_{1-3}$-Aryl-aminosulfonyl, $(R^8)_{1-3}$-Aryl-sulfonylamino, Het-amino, Het-sulfonyl, Het-aminosulfonyl, aminoiminoamino, or aminoiminoaminosulfonyl, where $R^7$, $R^8$, Aryl and Het are as defined below;

$R^5$ is hydrogen;

and further wherein $R^4$ and $R^5$ are optionally joined to form a fused ring, said ring selected from the group as defined for Het above, or any of said used rings optionally substituted by oxo or dioxo;

$R^6$ is hydrogen, $C_{1-6}$ aliphatic, hydroxy, $C_{1-6}$ alkoxy, or halogen;

$R^7$ is hydrogen, $C_{1-12}$ aliphatic, $C_{1-12}$ alkoxy, hydroxy-$C_{1-12}$ alkoxy, hydroxy-$C_{1-12}$ aliphatic, carboxylic acid, $C_{1-12}$ aliphatic-carbonyl, Het, Het-$C_{1-12}$-aliphatic, Het-$C_{1-12}$-alkoxy, di-Het-$C_{1-12}$-alkoxy Aryl, Aryl-$C_{1-12}$-aliphatic, Aryl-$C_{1-12}$-alkoxy, Aryl-carbonyl, $C_{1-18}$ alkoxyalkoxyalkoxyalkoxyaliphatic, or hydroxyl where Het and Aryl are as defined below;

$R^8$ is hydrogen or halo-$C_{1-6}$ aliphatic;

Aryl is phenyl, or naphthyl;

Cyc is cyclopropyl, cyclobutyl, cyclopentyl, cyclohexyl, cycloheptyl or cyclooctyl, any one of which may have one or more degrees of unsaturation;

Het is a saturated or unsaturated heteroatom ring system selected from the group consisting of benzimidazole, dihydrothiophene, dioxin, dioxane, dioxolane, dithiane, dithiazine, dithiazole, dithiolane, furan, imidazole, morpholine, oxazole, oxadiazole, oxathiazole, oxathiazolidine, oxazine, oxadiazine, piperazine, piperadine, pyran, pyrazine, pyrazole, pyridine, pyrimidine, pyrrole, pyrrolidine, tetrahydrofuran, tetrazine, thiadiazine, thiadiazole, thiatriazole, thiazine, thiazole, thiomorpholine, thiophene, thiopyran, triazine and triazole with the proviso that when $R^2$ is thiadiazine, then $R^4$ cannot be methylsulfone;

and the pharmaceutically acceptable salts, solvates, or physiologically functional derivatives thereof including biohydrolyzable esters, biohydrolyzable amides, biohydrolyzable carbamates, solvates, hydrates, affinity reagents or prodrugs thereof in either crystalline or amorphous form.

In a further aspect of the present invention, there is provided compounds of formula (I):

wherein

X is N, CH, or CCH$_3$;

$R^1$ is hydrogen, $C_{1-6}$ aliphatic, hydroxy-$C_{1-6}$ aliphatic, di-$C_{1-6}$ aliphatic amino, di-$C_{1-6}$ aliphatic aminocarbonyl, di-$C_{1-6}$ aliphatic aminosulfonyl, Aryl-$C_{1-6}$ aliphatic, $R^6$-Aryl-$C_{1-6}$ aliphatic, Cyc-$C_{1-6}$ aliphatic, Het-$C_{1-6}$ aliphatic, $C_{1-6}$ alkoxy, Aryloxy, aminocarbonyl, $C_{1-6}$ alkoxycarbonyl, halogen, or nitro, where $R^6$, Aryl, Cyc and Het are as defined below;

$R^2$ is hydrogen, $C_{1-6}$ aliphatic, N-hydroxyimino-$C_{1-6}$ aliphatic, $C_{1-6}$alkoxy, $C_{1-6}$ alkoxycarbonyl, Aryl, $R^6$-Aryloxy-carbonyl, Het, aminocarbonyl, $C_{1-6}$ aliphatic aminocarbonyl, Aryl-$C_{1-6}$ aliphatic aminocarbonyl, $R^6$-Aryl-$C_{1-6}$ aliphatic aminocarbonyl, Het-$C_{1-6}$ aliphatic aminocarbonyl, di-$C_{1-6}$ aliphatic amino, di-$C_{1-6}$ aliphatic aminocarbonyl, di-$C_{1-6}$ aliphatic aminosulfonyl, hydroxy-$C_{1-6}$ aliphatic aminocarbonyl, $C_{1-6}$-alkoxy-$C_{1-6}$ aliphatic aminocarbonyl, $C_{1-6}$ alkoxy-$C_{1-6}$ aliphatic amino, halogen, hydroxy, nitro, $C_{1-6}$ aliphatic sulfonyl, or aminosulfonyl, $C_{1-6}$ aliphatic aminosulfonyl, where Aryl and Het are as defined below;

further wherein $R^1$ and $R^2$ are optionally joined to form a fused ring, said fused ring selected from the group as defined for Het below, or any of said fused rings optionally substituted by halogen or oxo;

$R^3$ is hydrogen, $C_{1-6}$ aliphatic, hydroxy, hydroxy $C_{1-6}$ aliphatic, di-$C_{1-6}$ aliphatic amino, di-$C_{1-6}$ aliphatic aminocarbonyl, di-$C_{1-6}$ aliphatic aminosulfonyl $C_{1-6}$ alkoxy, Aryloxy, Het, or halogen, where Aryl and Het are as defined below;

further wherein $R^2$ and $R^3$ are optionally joined to form a fused ring, said fused ring selected from the group as defined for Het below, or any of said fused rings optionally substituted by $C_{1-6}$ alkyl or $C_{1-6}$ alkylcarbonyl;

$R^4$ is $R^7$-sulfonyl, $R^7$-sulfonyl $C_{1-6}$-aliphatic, $C_{1-6}$ aliphatic sulfonyl-$C_{1-6}$ aliphatic, $R^7$-aminosulfonyl, di-$C_{1-6}$ aliphatic amino, di-$C_{1-6}$ aliphatic aminocarbonyl, di-$C_{1-6}$ aliphatic aminosulfonyl, di-$C_{1-6}$ aliphatic aminosulfonyl-$C_{1-6}$ aliphatic, aminosulfonyl-$C_1$-$C_{12}$-aliphatic, $R^7$-aminosulfonyl $C_{1-6}$ aliphatic, aminosulfonylamino, $R^7$—$C_{1-6}$ aliphatic aminosulfonyl-$C_{1-6}$ aliphatic, Aryl, Het, $R^8$-Aryl-aminosulfonyl, Het-aminosulfonyl, or aminoiminoaminosulfonyl, where $R^7$, $R^8$, Aryl and Het are as defined below;

$R^5$ is hydrogen;

and further wherein $R^4$ and $R^5$ are optionally joined to form a fused ring, said ring selected from the group as defined for Het below, or any of said used rings optionally substituted by oxo or dioxo;

$R^6$ is hydroxy, $C_{1-6}$ alkoxy, or halogen;

$R^7$ is hydrogen, $C_{1-6}$ aliphatic, hydroxy $C_{1-6}$-alkoxy, hydroxy-$C_{1-6}$ aliphatic, $C_{1-6}$ aliphatic carbonyl, Aryl-carbonyl, $C_{1-12}$ alkoxyalkoxyalkoxyalkyl, hydroxyl, Aryl, Aryl-$C_{1-6}$-alkoxy, Aryl-$C_{1-6}$-aliphatic, Het, Het-$C_{1-6}$-alkoxy, di-Het-$C_{1-6}$-alkoxy, Het-$C_{1-6}$-aliphatic, di-Het-$C_{1-6}$-aliphatic;

$R^8$ is trifluoromethyl;

Aryl is phenyl;

Cyc is cyclobutyl;

Het is a saturated or unsaturated heteroatom ring system selected from the group consisting of benzimidazole, dihydrothiophene, dioxolane, furan, imidazole, morpholine, oxazole, pyridine, pyrrole, pyrrolidine, thiadiazole, thiazole, thiophene, and triazole, with the proviso that when $R^2$ is thiadiazine, then $R^4$ cannot be methylsulfone;

and the pharmaceutically acceptable salts, solvates, physiologically functional derivatives thereof, including biohydrolyzable esters, biohydrolyzable amides, biohydrolyzable carbamates, solvates, hydrates, affinity reagents or prodrugs thereof in either crystalline or amorphous form.

In a still further aspect of the present invention, there is provided compounds of formula (I):

wherein

X is CH;

$R^1$ is hydrogen, $C_{1-12}$ aliphatic, thiol, hydroxy, hydroxy-$C_{1-12}$ aliphatic, Aryl, Aryl-$C_{1-12}$ aliphatic, $R^6$-Aryl-$C_{1-12}$ aliphatic, Cyc, Cyc-$C_{1-6}$ aliphatic, Het, Het-$C_{1-12}$ aliphatic, $C_{1-12}$ alkoxy, Aryloxy, amino, $C_{1-12}$ aliphatic amino, di-$C_{1-12}$ aliphatic amino, di-$C_{1-12}$ aliphatic aminocarbonyl, di-$C_{1-12}$ aliphatic aminosulfonyl, $C_{1-12}$ alkoxycarbonyl, halogen, cyano, sulfonamide, or nitro, where $R^6$, Aryl, Cyc and Het are as defined below;

$R^2$ is hydrogen, $C_{1-12}$ aliphatic, N-hydroxyimino-$C_{1-12}$ aliphatic, $C_{1-12}$ alkoxy, hydroxy-$C_{1-12}$ aliphatic, $C_{1-12}$ alkoxycarbonyl, carboxyl $C_{1-12}$ aliphatic, Aryl, $R^6$-Aryl-oxycarbonyl, $R^6$-oxycarbonyl-Aryl, Het, aminocarbonyl, $C_{1-12}$ aliphatic-aminocarbonyl, Aryl-$C_{1-12}$ aliphatic-aminocarbonyl, $R^6$-Aryl-$C_{1-12}$ aliphatic-aminocarbonyl, Het-$C_{1-12}$ aliphatic-aminocarbonyl, hydroxy-$C_{1-12}$ aliphatic-aminocarbonyl, $C_{1-12}$-alkoxy-$C_{1-12}$ aliphatic-aminocarbonyl, $C_{1-12}$ alkoxy-$C_{1-12}$ aliphatic-amino, di-$C_{1-12}$ aliphatic amino, di-$C_{1-12}$ aliphatic aminocarbonyl, di-$C_{1-12}$ aliphatic aminosulfonyl, halogen, hydroxy, nitro, $C_{1-12}$ aliphatic-sulfonyl, aminosulfonyl, or $C_{1-12}$ aliphatic-aminosulfonyl, where Aryl and Het are as defined below;

further wherein $R^1$ and $R^2$ are optionally joined to form a fused ring, said fused ring selected from the group as defined for Het below, or any of said fused rings optionally substituted by halogen, nitro, cyano, $C_{1-12}$ alkoxy, carbonyl-$C_{1-12}$ alkoxy or oxo;

$R^3$ is hydrogen, $C_{1-12}$ aliphatic, hydroxy, hydroxy $C_{1-12}$ aliphatic, di-$C_{1-12}$ aliphatic amino, di-$C_{1-12}$ aliphatic aminocarbonyl, di-$C_{1-12}$ aliphatic aminosulfonyl, $C_{1-12}$ alkoxy, Aryl, Aryloxy, hydroxy-Aryl, Het, hydroxy-Het, Het-oxy, or halogen, where Aryl and Het are as defined below;

further wherein $R^2$ and $R^3$ are optionally joined to form a fused ring, said fused ring selected from the group as defined for Het below, or any of said fused rings optionally substituted by $C_{1-6}$ aliphatic or $C_{1-6}$ aliphatic-carbonyl;

$R^4$ is $R^7$-aminosulfonyl, $R^7$-aminosulfonyl-$C_{1-12}$ aliphatic, $R^7$-sulfonylamino, $R^7$-sulfonylamino-$C_{1-12}$ aliphatic, aminosulfonylamino, di-$C_{1-12}$ aliphatic aminosulfonyl, di-$C_{1-12}$ aliphatic aminosulfonyl-$C_{1-12}$ aliphatic, $(R^8)_{1-3}$-Aryl-aminosulfonyl, aminosulfonyl-$C_1$-$C_{12}$-aliphatic, $(R^8)_{1-3}$-Aryl-sulfonylamino, or aminoiminoaminosulfonyl, where $R^7$, $R^8$, Aryl and Het are as defined below;

$R^5$ is hydrogen;

$R^6$ is $C_{1-12}$ aliphatic, hydroxy, $C_{1-12}$ alkoxy, or halogen;

$R^7$ is hydrogen, $C_{1-12}$ aliphatic, $C_{1-12}$ alkoxy, hydroxy-$C_{1-12}$ alkoxy, hydroxy-$C_{1-12}$ aliphatic, carboxylic acid, $C_{1-12}$ aliphatic-carbonyl, Het, Het-$C_{1-12}$-aliphatic, Het-$C_{1-12}$-alkoxy, di-Het-$C_{1-12}$-alkoxy Aryl, Aryl-$C_{1-12}$-aliphatic, Aryl-$C_{1-12}$-alkoxy, Aryl-carbonyl, $C_{1-18}$ alkoxyalkoxyalkoxyalkoxy-aliphatic, or hydroxyl where Het and Aryl are as defined below;

$R^8$ is hydrogen, nitro, cyano, $C_{1-12}$ alkoxy, halo, carbonyl-$C_{1-12}$ alkoxy or halo-$C_{1-12}$ aliphatic;

Aryl is phenyl, naphthyl, phenanthryl or anthracenyl;

Cyc is cyclopropyl, cyclobutyl, cyclopentyl, cyclohexyl, cycloheptyl or cyclooctyl, any one of which may have one or more degrees of unsaturation;

Het is a saturated or unsaturated heteroatom ring system selected from the group consisting of benzimidazole, dihydrothiophene, dioxin, dioxane, dioxolane, dithiane, dithiazine, dithiazole, dithiolane, furan, imidazole, morpholine, oxazole, oxadiazole, oxathiazole, oxathiazolidine, oxazine, oxadiazine, piperazine, piperadine, pyran, pyrazine, pyrazole, pyridine, pyrimidine, pyrrole, pyrrolidine, tetrahydrofuran, tetrazine, thiadiazine, thiadiazole, thiatriazole, thiazine, thiazole, thiomorpholine, thiophene, thiopyran, triazine and triazole with the proviso that when $R^2$ is thiadiazine, then $R^4$ cannot be methylsulfone;

and the pharmaceutically acceptable salts, solvates, physiologically functional derivatives thereof, including biohydrolyzable esters, biohydrolyzable amides, biohydrolyzable carbamates solvates, hydrates, affinity reagents or prodrugs thereof in either crystalline or amorphous form.

In another aspect of the present invention, there is provided a compound of the formula I, or salts, solvates, or physiological functional derivatives thereof wherein:

$R^1$ is hydrogen or halogen;

$R^2$ is hydrogen, hydroxy or methoxy;

$R^3$ is hydrogen or $C_1$-$C_6$ branched alkyl;

$R^4$ is selected from the group consisting of
4'—$CH_2$—$SO_2NHCH_3$, 4'—$NHSO_2CH_3$,

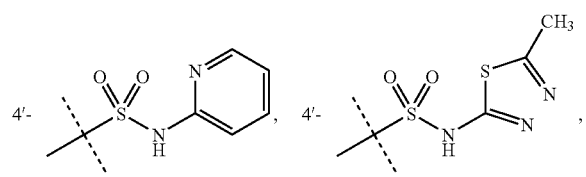

or 3'—$SO_2NH_2$;

$R^5$ is hydrogen; and

X is N or CH.

Due to the presence of an oxindole exocyclic double bond, also included in the compounds of the invention are their respective pure E and Z geometric isomers as well as mixtures of E and Z isomers. The invention as described and claimed does not set any limiting ratios on prevalence of Z to E isomers. Thus compound number 104 in the tables below is disclosed and claimed as the E geometric thereof, the Z geometric isomer thereof and a mixture of the E and Z geometric isomers thereof, but not limited by any given ratio(s).

Likewise, it is understood that compounds of formula (I) may exist in tautomeric forms other than that shown in the formula.

Certain of the compounds as described will contain one or more chiral, or asymmetric, centers and will therefore be capable of existing as optical isomers that are either dextrorotatory or levorotatory. Also included in the compounds of the invention are the respective dextrorotatory or levorotatory pure preparations, and mixtures thereof.

Certain compounds of formula (I) above may exist in stereoisomeric forms (e.g. they may contain one or more asymmetric carbon atoms or may exhibit cis-trans isomerism). The individual stereoisomers (enantiomers and diastereoisomers) and mixtures of these are included within the scope of the present invention. Likewise, it is understood that compounds of formula (I) may exist in tautomeric forms other than that shown in the formula and these are also included within the scope of the present invention.

A further aspect of the invention provides a method of treating a disorder in a mammal, said disorder mediated by inappropriate mitogen activated kinase activity, including administering to said mammal a therapeutically effective amount of a compound of formula (I) or a salt, solvate, or physiologically functional derivative thereof. In one embodiment, the disorder is cancer. In another embodiment the disorder is chronic pain. In a further embodiment, the disorder involves abnormal angiogenesis, such as arthritis, diabetic retinopathy, macular degeneration and psoriasis.

In a related aspect the present invention comprises a method for inhibiting a kinase comprising bringing said kinase into contact with a compound of formula (I), or a salt, solvate, or physiologically functional derivative thereof.

Another aspect of the present invention provides for the use of a compound of formula (I), or a salt, solvate, or physiologically functional derivative thereof, in the preparation of a medicament for the treatment of a disorder mediated by inappropriate TrkA activity. In one embodiment, the disorder is cancer. In another embodiment, the disorder is chronic pain. In a further embodiment, the disorder involves abnormal angiogenesis, such as arthritis, diabetic retinopathy, macular degeneration and psoriasis.

Additionally, compounds of formula (I) or salts, solvates, or physiologically functional derivatives thereof, can be used in the preparation of a medicament for the treatment of organ transplant rejection, tumor growth, chemotherapy-induced mucositis, radiation-induced mucositis, plantar-palmar syndrome, chemotherapy-induced alopecia, chemotherapy-induced thrombocytopenia, chemotherapy-induced leukopenia and hirsutism or of treating a disease state selected from the group consisting of: mucositis, restenosis, atherosclerosis, rheumatoid arthritis, angiogenesis, hepatic cirrhosis, glomerulonephritis, diabetic nephropathy, malignant nephrosclerosis, chronic obstructive pulmonary disease, thrombotic microangiopathy, aglomerulopathy, psoriasis, diabetes mellitus, inflammation, a neurodegenerative disease, macular degeneration, actinic keratosis and hyperproliferative disorders.

Another aspect of the present invention provides the use of an active compound of formula (I), in co-administration or alternating administration with previously known anti-tumor therapies for more effective treatment of such tumors.

Other aspects of the present invention related to the inhibition of protein kinases are discussed in more detail below.

The inappropriate TrkA activity referred to herein is any TrkA activity that deviates from the normal TrkA activity expected in a particular mammalian subject. Inappropriate TrkA activity may take the form of, for instance, an abnormal increase in activity, or an aberration in the timing and or control of TrkA activity. Such inappropriate activity may result then, for example, from overexpression or mutation of the protein kinase leading to inappropriate or uncontrolled activation. Furthermore, it is also understood that unwanted TrkA activity may reside in an abnormal source, such as a malignancy. That is, the level of TrkA activity does not have to be abnormal to be considered inappropriate, rather the activity derives from an abnormal source.

Compounds we have synthesized as part of the present invention which are currently preferred are listed in Tables 1 and 2 below. Compounds are identified by the numbers shown in the first column; variables below in the rest of the columns are with reference to the generic structure (I). Corresponding IUPAC nomenclature are disclosed in Table 2. Since all substituents at each point of substitution are capable of independent synthesis of each other, the tables are to be read as a matrix in which any combination of substituents is within the scope of the disclosure and claims of the invention.

TABLE 1

(I)

[Structure of formula (I): indol-2-one with substituents R¹, R², R³ at positions 4,5,6 of indole; at position 3, =X—NH—phenyl with R⁴, R⁵ substituents]

| Example | R¹ | R² | R³ | R⁴ | R⁵ | X |
|---|---|---|---|---|---|---|
| 1 | Cl | OH | i-propyl | 4'-CH₂—SO₂NHCH₃ | H | N |
| 2 | —H | H | H | 4'-NHSO₂CH₃ | H | CH |
| 3 | —H | H | H | 4'- [SO₂NH-(2-pyridinyl)] | H | CH |
| 4 | —H | H | H | 4'- [SO₂NH-(5-methyl-1,3,4-thiadiazol-2-yl)] | H | CH |
| 5 | —H | H | H | 3'-SO₂NH₂ | H | CH |

Standard accepted nomenclature corresponding to the Examples set forth in this specification are set forth below. In some cases nomenclature is given for one or more possible isomers.

TABLE II

Example 1: {4-[(2Z)-2-(4-chloro-5-hydroxy-6-isopropyl-2-oxo-1,2-dihydro-3H-indol-3-ylidene)hydrazino]phenyl}-N-methylmethanesulfonamide Example 2: N-(4-{[(Z)-(2-oxo-1,2-dihydro-3H-indol-3-ylidene)methyl]amino}phenyl)methanesulfonamide Example 3: 4-{[(Z)-(2-oxo-1,2-dihydro-3H-indol-3-ylidene)methyl]amino}-N-(2-pyridinyl)benzenesulfonamide Example 4: N-(5-methyl-1,3,4-thiadiazol-2-yl)-4-{[(Z)-(2-oxo-1,2-dihydro-3H-indol-3-ylidene)methyl]amino}benzenesulfonamide Example 5: 3-{[(Z)-(2-oxo-1,2-dihydro-3H-indol-3-ylidene)methyl]amino}benzenesulfonamide The invention discloses six different points of substitution on structural formula (I). Each of these points of substitution bears a substituent whose selection and synthesis as part of this invention was independent of all other points of substitution on formula (I). Thus, each point of substitution is now further described individually.

Preferred substitutions at the R¹ position include hydrogen, halogen, amide, nitro, lower alkyl, hydroxy, hydroxyalkyl, pyrimidineloweralkyl, loweralkoxycarbonyl, cyclic loweralkyl, hydroxyphenylloweralkyl, phenoxy, alkoxy, or pyrazole, or are fused with R² to form fused thiazole, pyrazole, triazole, halogen-substituted diazole, acyl substituted pyrrole, and pyridine, rings. Most preferred are hydrogen, halogen, methyl and fused with R² for form fused thiazole and fused pyridine. Most highly preferred are halogen and hydrogen.

Preferred substitutions at the R² position include hydrogen, halogen, hydroxyl, sulfate, amine, quaternary amine, amide, ester, phenyl, alkoxy, aminosulfonyl, lower alkyl sulfonyl, furanyl lower alkyl amide, pyridinyl lower alkyl amide, alkoxy-substituted phenyl lower alkyl amide, morpholino lower alkyl amide, imidazolyl lower alkyl amide, hydroxy lower alkyl amide, alkoxy lower alkyl amide, lower alkyl amide, lower alkyl sulfonamide, lower alkyl hydroxy substituted amino, nitro, halogen-substituted phenoxycarbonyl, or triazole or oxazole rings, or are fused with R³ to form a fused oxazole, pyrrole, or dioxolane ring, which fused rings can be substituted by lower alkyl, lower alkyl carbonyl, or, when said fused ring is a hetero ring having nitrogen as the heteroatom, forming a quaternary ammonium salt ionically bonded with a halogen atom. Most preferred are hydrogen, hydroxyl, oxazolyl, lower alkoxy, or fused with R¹ to form fused thiazolyl or fused pyridyl Most highly preferred are hydroxy, methoxy and hydrogen.

Preferred substitutions at R³ include hydrogen, lower alkyl, hydroxy lower alkyl, halogen, phenoxy, and alkoxy. Most preferred are hydrogen and branched lower alkyl. Most highly preferred is hydrogen and isopropyl.

Preferred substitutions at R⁴ include sulfonylamino, sulfonylaminoamino, lower alkyl sulfonylamino, lower alkylsulfonyl lower alkyl, alkoxysulfonylamino, phenylcarbonylsulfonylamino, phenoxysulfonyl, hydroxy lower alkylsulfonylamino, hydroxy lower alkylsulfonylamino lower alkyl, alkyl, phenylsulfonylamino, optionally substituted by halogen substituted lower alkyl, aminoiminosulfonylamino, alkylsulfonylaminoalkyl, pyridinyl lower alkyl sulfonylamino, benzamideazolesulfonylamino, pyridylsulfonylamino, pyrimidinylsulfonylamino, thiadiazolylsulfonylamino optionally substituted by lower alkyl, thiazolesulfonylamino, -aminosulfonyl-$C_1$-$C_{12}$-aliphatic, hydroxyalkoxyalkylsulfonylamino, or the group 4'-SO₂NH[(CH₂)₂O]₄CH₃, or are fused with R⁵ to form a fused imidazole, triazole, cyclic sulfonylamino or thiaphene ring optionally disubstituted on the sulfur heteroatom by oxo. The most preferred substitutions are 2 pyridine sulfonylamino, 4 pyridine sulfonylamino, hydroxy n-butyl sulfonylamino, methylsulfonylaminomethylene, sulfonyldimethylamino, fused 1,2,3-triazole, and sulfonylamino. Most highly preferred is 2 pyridine sulfonylamino, 4 pyridine sulfonylamino and hydroxy n-butyl sulfonylamino. In an alternate highly preferred embodiment, R4 is 4'—CH₂—SO₂NHCH₃, 4'—NHSO₂CH₃,

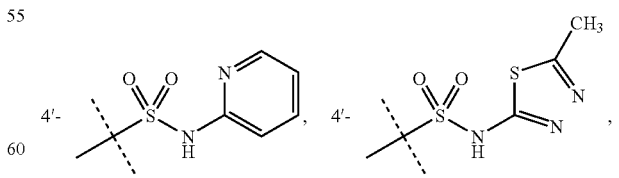

or 3'—SO₂NH₂;

The preferred substitution at R⁵ is hydrogen.

Preferred substitutions at X include N, CH, and CCH₃. Most preferred is N and CH.

Preferred individual compounds of the present invention include any one of the following compounds:

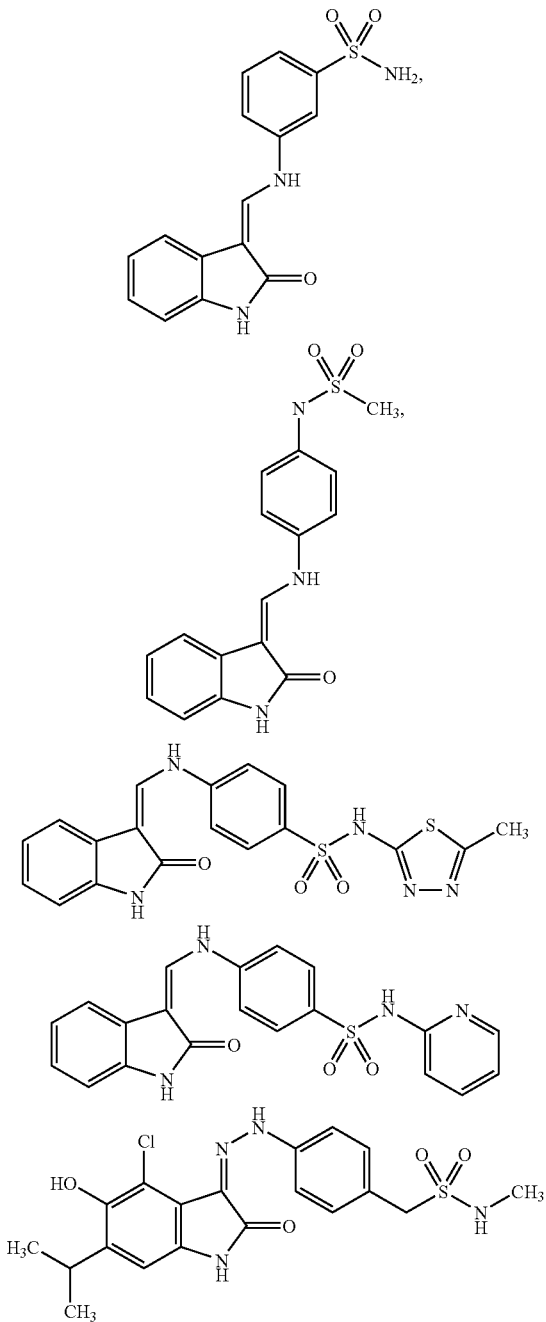

DETAILED DESCRIPTION OF THE INVENTION

Salts encompassed within the term "pharmaceutically acceptable salts" refer to non-toxic salts of the compounds of this invention which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Diethanolamine, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrocloride, Hydroxynaphthoate, Iodide, Isethionate, Lactate, Lactobionate, Laurate, Malate, Maleate, Mandelate, Mesylate, Metaphosphoric, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphateldiphosphate, Polygalacturonate, Potassium, Salicylate, Sodium, Stearate, Subacetate, Succinate, Tannate, Tartrate, Teoclate, Tosylate, Trifluoroacetate, Triethiodide, Trimethylammonium and Valerate.

Other salts which are not pharmaceutically acceptable may be useful in the preparation of compounds of formula (I) and these form a further aspect of the invention.

Also included within the scope of the invention are the individual isomers of the compounds represented by formula (I) above as well as any wholly or partially equilibrated mixtures thereof. The present invention also covers the individual isomers of the compounds represented by formula above as mixtures with isomers thereof in which one or more chiral asymmetric centers are inverted.

As used herein, the term "aliphatic" refers to the terms alkyl, alkylene, alkenyl, alkenylene, alkynyl, and alkynylene.

As used herein, the term "lower" refers to a group having between one and six carbons.

As used herein, the term "alkyl" refers to a straight or branched chain hydrocarbon having from one to twelve carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkyl" as used herein include, but are not limited to, n-butyl, n-pentyl, isobutyl, and isopropyl, and the like.

As used herein, the term "alkylene" refers to a straight or branched chain divalent hydrocarbon radical having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkylene" as used herein include, but are not limited to, methylene, ethylene, and the like.

As used herein, the term "alkenyl" refers to a hydrocarbon radical having from two to ten carbons and at least one carbon-carbon double bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed.

As used herein, the term "alkenylene" refers to a straight or branched chain divalent hydrocarbon radical having from two to ten carbon atoms and one or more carbon-carbon double bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkenylene" as used herein include, but are not limited to, ethene-1,2-diyl, propene-1,3-diyl, methylene-1,1-diyl, and the like.

As used herein, the term "alkynyl" refers to a hydrocarbon radical having from two to ten carbons and at least one carbon-carbon triple bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed.

As used herein, the term "alkynylene" refers to a straight or branched chain divalent hydrocarbon radical having from two to ten carbon atoms and one or more carbon-carbon triple bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkynylene" as used herein include, but are not limited to, ethyne-1,2-diyl, propyne-1,3-diyl, and the like.

As used herein, the term "cycloaliphatic" refers to the terms cycloalkyl, cycloalkylene, cycloalkenyl, cycloalkenylene, cycloalkynyl and cycloalkylnylene.

As used herein, "cycloalkyl" refers to a alicyclic hydrocarbon group with one or more degrees of unsaturation, having from three to twelve carton atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes by way of example cyclopropyl, cyclobutyl, cyclopentyl, cyclohexyl, cycloheptyl, or cyclooctyl, and the like.

As used herein, the term "cycloalkylene" refers to an non-aromatic alicyclic divalent hydrocarbon radical having from three to twelve carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "cycloalkenyl" refers to a substituted alicyclic hydrocarbon radical having from three to twelve carbon atoms and at least one carbon-carbon double bond in the ring system, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkenylene" as used herein include, but are not limited to, 1-cyclopentene-3-yl, 1-cyclohexene-3-yl, 1-cycloheptene-4-yl, and the like.

As used herein, the term "cycloalkenylene" refers to a substituted alicyclic divalent hydrocarbon radical having from three to twelve carbon atoms and at least one carbon-carbon double bond in the ring system, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkenylene" as used herein include, but are not limited to, 4,5-cyclopentene-1,3-diyl, 3,4-cyclohexene-1,1-diyl, and the like.

As used herein, the term "heteroatom ring system" refers to the terms heterocyclic, heterocyclyl, heteroaryl, and heteroarylene. Non-limiting examples of such heteroatom ring systems are recited in the Summary of the Invention, above.

As used herein, the term "heterocyclic" or the term "heterocyclyl" refers to a three to twelve-membered heterocyclic ring having one or more degrees of unsaturation containing one or more heteroatomic substitutions selected from S, SO, $SO_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more of another "heterocyclic" ring(s) or cycloalkyl ring(s). Examples of "heterocyclic" include, but are not limited to, tetrahydrofuran, pyran, 1,4-dioxane, 1,3-dioxane, piperidine, pyrrolidine, morpholine, tetrahydrothiopyran, tetrahydrothiophene, and the like.

As used herein, the term "heterocyclylene" refers to a three to twelve-membered heterocyclic ring diradical having one or more degrees of unsaturation containing one or more heteroatoms selected from S, SO, $SO_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, and the like.

As used herein, the term "aryl" refers to a benzene ring or to an optionally substituted benzene ring system fused to one or more optionally substituted benzene rings to form anthracene, phenanthrene, or napthalene ring systems, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. Examples of aryl include, but are not limited to, phenyl, 2-naphthyl, 1-naphthyl, biphenyl, and the like.

As used herein, the term "arylene" refers to a benzene ring diradical or to a benzene ring system diradical fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. Examples of "arylene" include, but are not limited to, benzene-1,4-diyl, naphthalene-1,8-diyl, anthracene-1,4-diyl, and the like.

As used herein, the term "heteroaryl" refers to a five- to seven-membered aromatic ring, or to a polycyclic heterocyclic aromatic ring, containing one or more nitrogen, oxygen, or sulfur heteroatoms at any position, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole, and the like.

As used herein, the term "heteroarylene" refers to a five- to seven-membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "alkoxy" refers to the group $R_aO$—, where $R_a$ is aliphatic.

As used herein, the term "alkylsulfanyl" refers to the group $R_aS$—, where $R_a$ is aliphatic.

As used herein, the term "alkylsulfenyl" refers to the group $R_aS(O)$—, where $R_a$ is aliphatic.

As used herein, the term "alkylsulfonyl" refers to the group $R_aSO_2$—, where $R_a$ is aliphatic.

As used herein, the term "acyl" refers to the group $R_aC(O)$—, where $R_a$ is aliphatic, cycloaliphatic, or heterocyclyl.

As used herein, the term "aroyl" refers to the group $R_aC(O)$—, where $R_a$ is aryl.

As used herein, the term "heteroaroyl" refers to the group $R_aC(O)$—, where $R_a$ is heteroaryl.

As used herein, the term "alkoxycarbonyl" refers to the group $R_aOC(O)$—, where $R_a$ is aliphatic.

As used herein, the term "acyloxy" refers to the group $R_aC(O)O$—, where $R_a$ is aliphatic, cycloaliphatic, or heterocyclyl.

As used herein, the term "aroyloxy" refers to the group $R_aC(O)O$—, where $R_a$ is aryl.

As used herein, the term "heteroaroyloxy" refers to the group $R_aC(O)O$—, where $R_a$ is heteroaryl.

As used herein, the term "optionally" means that the subsequently described event(s) may or may not occur, and includes both conditions.

As used herein, the term "substituted" refers to substitution with the named substituent or substituents, multiple degrees of substitution being allowed.

As used herein, the terms "contain" or "containing" can refer to in-line substitutions at any position along the above-defined alkyl, alkenyl, alkynyl or cycloalkyl substituents with one or more of any of O, S, SO, $SO_2$, N, or N-alkyl, including, for example, —$CH_2$—O—$CH_2$—, —$CH_2$—$SO_2$—$CH_2$—, —$CH_2$—NH—$CH_3$ and so forth.

As used herein, the term "solvate" is a complex of variable stoichiometry formed by a solute (in this invention, a compound of formula (I)) and a solvent. Such solvents for the purpose of the invention may not interfere with the biological activity of the solute. Solvents may be, by way of example, water, ethanol, or acetic acid.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, $5^{th}$ Edition, Vol 1: Principles and Practice, which is incorporated herein by reference to the extent that it teaches physiologically functional derivatives. Included within the scope of the term are the terms "biohydrolyzable carbonate", "biohydrolyzable ureide", "biohydrolyzable carbamate", "biohydrolyzable ester", and "biohydrolyzable amide".

As used herein, the terms "biohydrolyzable carbonate", "biohydrolyzable ureide" and "biohydrolyzable carbamate" is a carbonate, ureide, or carbamate, respectively of a drug substance (in this invention, a compound of general formula (I) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable carbamate is orally absorbed from the gut and is transformed to (I) in plasma. Many examples of such are known in the art and include by way of example lower alkyl carbamates.

As used herein, the term "biohydrolyzable ester" is an ester of a drug substance (in this invention, a compound of general formula (I) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is transformed to (I) in plasma. Many examples of such are known in the art and include by way of example lower alkyl esters, lower acyloxy-alkyl esters, lower alkoxyacyloxyalkyl esters, alkoxyacyloxy esters, alkyl acylamino alkyl esters, and choline esters.

As used herein, the term "biohydrolyzable amide" is an amide of a drug substance (in this invention, a compound of general formula (I) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to (I) in plasma. Many examples of such are known in the art and include by way of example lower alkyl amides, α-amino acid amides, alkoxyacyl amides, and alkylaminoalkylcarbonyl amides.

As used herein, the term "prodrug" includes biohydrolyzable amides, biohydrolyzable esters and biohydrolyzable carbamates and also encompasses a) compounds in which the biohydrolyzable functionality in such a prodrug is encompassed in the compound of formula (I): for example, a lactam formed by a carboxylic group in $R_1$ and an amine in $R_2$, and compounds which may be oxidized or reduced biologically at a given functional group to yield drug substances of formula (I). Examples of these functional groups are, but are not limited to, 1,4-dihydropyridine, N-alkylcarbonyl-1,4-dihydropyridine, 1,4-cyclohexadiene, tert-butyl, and the like.

As used herein, the term "affinity reagent" is a group attached to the compound of formula (I) which does not affect its in vitro biological activity, allowing the compound to bind to a target, yet such a group binds strongly to a third component allowing a) characterization of the target as to localization within a cell or other organism component, perhaps by visualization by fluorescence or radiography, or b) facile separation of the target from an unknown mixture of targets, whether proteinaceous or not proteinaceous. An example of an affinity reagent according to b) would be biotin either directly attached to (I) or linked with a spacer of one to 50 atoms selected from the group consisting of C, H, O, N, S, or P in any combination. An example of an affinity reagent according to a) above would be fluorescein, either directly attached to (I) or linked with a spacer of one to 50 atoms selected from the group consisting of C, H, O, N. S, or P in any combination.

The term "effective amount" means that amount of a drug or pharmaceutical agent that will elicit the biological or medical response of a tissue, system, animal or human that is being sought by a researcher or clinician. The term "therapeutically effective amount" means any amount which, as compared to a corresponding subject who has not received such amount, results in improved treatment, healing, prevention, or amelioration of a disease or disorder, or a decrease in the rate of advancement of a disease or disorder, and also includes amounts effective to enhance normal physiological function.

Whenever the terms "aliphatic" or "aryl" or either of their prefixes appear in a name of a substituent (e.g. arylalkoxyaryloxy) they shall be interpreted as including those limitations given above for "aliphatic" and "aryl". Aliphatic or cycloalkyl substituents shall be recognized as being term equivalents to those having one or more degrees of unsaturation. Designated numbers of carbon atoms (e.g. $C_{1-10}$) shall refer independently to the number of carbon atoms in an aliphatic or cyclic aliphatic moiety or to the aliphatic portion of a larger substituent in which the term "aliphatic" appears as a prefix (e.g. "al-").

As used herein, the term "disubstituted amine" or "disubstituted amino-" shall be interpreted to include either one or two substitutions on that particular nitrogen atom.

As used herein, the term "oxo" shall refer to the substituent =O.

As used herein, the term "halogen" or "halo" shall include iodine, bromine, chlorine and fluorine.

As used herein, the term "mercapto" shall refer to the substituent —SH.

As used herein, the term "carboxy" shall refer to the substituent —COOH.

As used herein, the term "cyano" shall refer to the substituent —CN.

As used herein, the term "aminosulfonyl" shall refer to the substituent —$SO_2NH_2$.

As used herein, the term "carbamoyl" shall refer to the substituent —$C(O)NH_2$.

As used herein, the term "sulfanyl" shall refer to the substituent —S—.

As used herein, the term "sulfenyl" shall refer to the substituent —S(O)—.

As used herein, the term "sulfonyl" shall refer to the substituent —$S(O)_2$—.

Pharmaceutical Formulation and Doses

While it is possible that, for use in therapy, therapeutically effective amounts of a compound of formula I, as well as salts, solvates and physiological functional derivatives thereof, may be administered as the raw chemical, it is possible to present the active ingredient as a pharmaceutical composition. Accordingly, the invention further provides pharmaceutical compositions which include therapeutically effective amounts of compounds of the formula I and salts, solvates and physiological functional derivatives thereof, and one or more pharmaceutically acceptable carriers, diluents, or excipients. The compounds of the formula I and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula I, or salts, solvates and physiological functional derivatives thereof, with one or more pharmaceutically acceptable carriers, diluents or excipients.

The compounds of the present invention can be administered in such oral (including buccal and sublingual) dosage forms as tablets, capsules (each including timed release and sustained release formulations), pills, powders, granules, elixirs, tinctures, suspensions, syrups and emulsions. Likewise, they may also be administered in nasal, ophthalmic, otic, rectal, topical, intravenous (both bolus and infusion), intraperitoneal, intraarticular, subcutaneous or intramuscular inhalation or insufflation form, all using forms well known to those of ordinary skill in the pharmaceutical arts.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.1 to 100 mg/kg of body weight per day, and particularly 1 to 10 mg/kg of body weight per day. Oral dosage units will generally be administered in the range of from 1 to about 250 mg and more preferably from about 25 to 250 mg. The daily dosage for a 70 kg mammal will generally be in the range of about 70 mg to 7 grams of a compound of formula I or II.

While the dosage to be administered is based on the usual conditions such as the physical condition of the patient, age, body weight, past medical history, route of administrations, severity of the conditions and the like, it is generally preferred for oral administration to administer to a human. In some cases, a lower dose is sufficient and, in some cases, a higher dose or more doses may be necessary. Topical application similarly may be once or more than once per day depending upon the usual medical considerations. Advantageously, compounds of the present invention may be administered in a single daily dose, or the total daily dosage may be administered in divided doses of two, three or four times daily. The compounds of the invention can be prepared in a range of concentrations for topical use of 0.5 to 5 mg/ml of suitable solvent. A preferred volume for application to the scalp is 2 ml, resulting in an effective dosage delivered to the patient of 1 to 10 mg. For treatment of chemotherapy-induced alopecia, administration 1 to 2 times prior to chemotherapy administration would be preferred, with additional applications administered as needed. A similar regimen can be pursued for treatment of alopecia induced by radiation therapy. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolyl-ysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, poly-orthoesters, polyacetals, polydihydropyrans, polycy-anoacrylates and cross-linked or amphipathic block copolymers of hydrogels.

The present invention includes pharmaceutical compositions containing 0.01 to 99.5%, more particularly, 0.5 to 90% of a compound of the formula (II) in combination with a pharmaceutically acceptable carrier.

Parenteral administration can be effected by utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as aqueous oleaginous medium and sterilizing the suspension or solution.

Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservations and emulsifiers can also be added.

Rectal administration can be effected utilizing suppositories in which the compound is admixed with low-melting water-soluble or insoluble solids such as polyethylene glycol, cocoa butter, higher ester as for example flavored aqueous solution, while elixirs are prepared through myristyl palmitate or mixtures thereof.

Topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams. The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

The preferred pharmaceutical compositions are those in a form suitable for oral administration, such as tablets and liquids and the like and topical formulations.

The compounds of formula (I) can be prepared readily according to the following reaction General Synthesis Scheme (in which all variables are as defined before) and Examples or modifications thereof using readily available starting materials, reagents and conventional synthesis procedures. In these reactions, it is also possible to make use of variants which are themselves known to those of ordinary skill in this art, but are not mentioned in greater detail.

General Synthesis Scheme

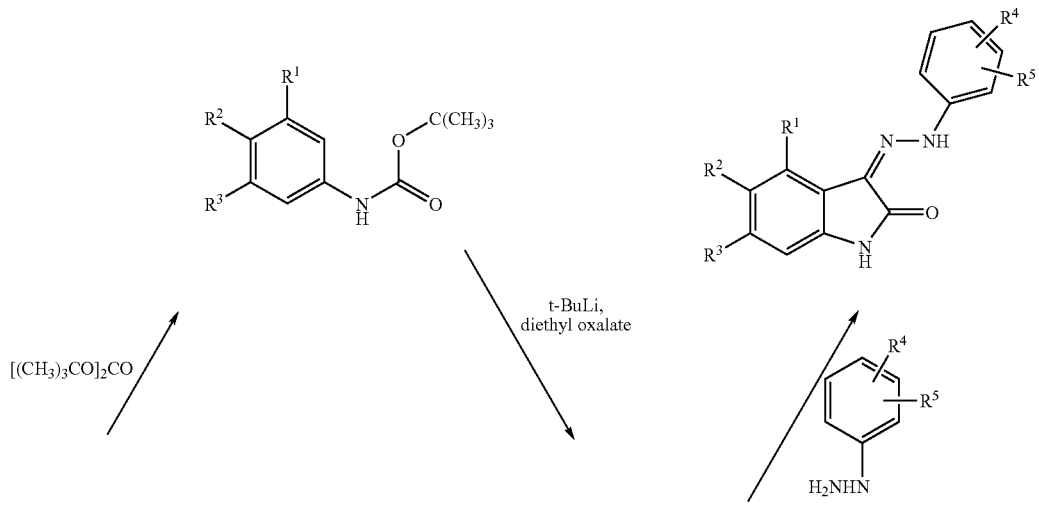

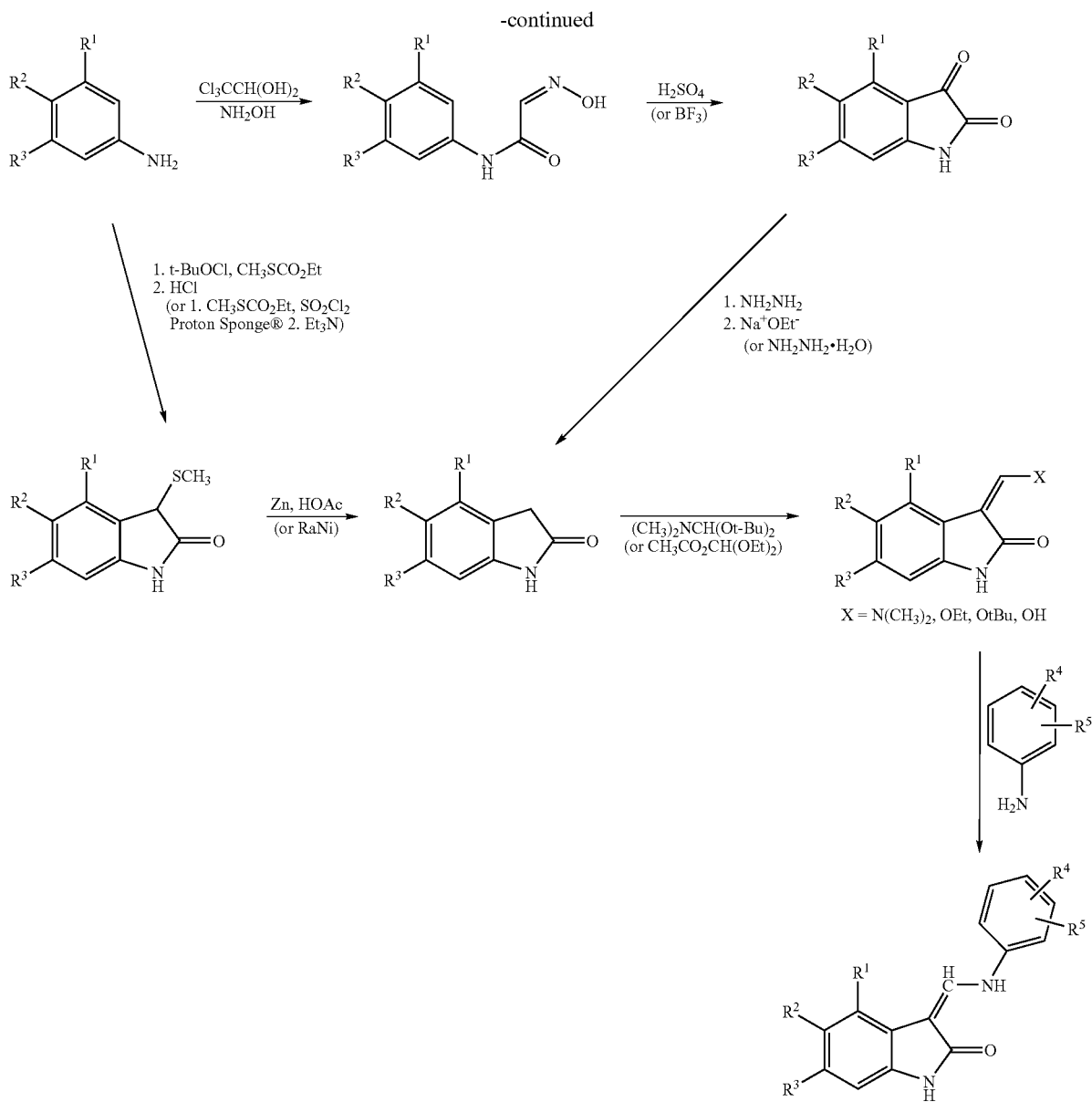

The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless noted otherwise.

Abbreviations used in the Examples are as follows:
g=grams
mg=milligrams
L=liters
mL=milliliters
M=molar
N=normal
mM=millimolar
i.v.=intravenous
p.o.=per oral
s.c.=subcutaneous
Hz=hertz
mol=moles
mmol=millimoles
mbar=millibar
psi=pounds per square inch
rt=room temperature
min=minutes
h=hours
mp=melting point
TLC=thin layer chromatography
$R_f$=relative TLC mobility
MS=mass spectrometry
NMR=nuclear magnetic resonance spectroscopy
APCI=atmospheric pressure chemical ionization
ESI=electrospray ionization
m/z=mass to charge ratio
$t_r$=retention time Pd/C=palladium on activated carbon
ether=diethyl ether
MeOH=methanol
EtOAc=ethyl acetate
TEA=triethylamine
DIEA=diisopropylethylamine
THF=tetrahydrofuran
DMF=N,N-dimethylformamide
DMSO=dimethylsulfoxide
DDQ=2,3-dichloro-5,6-dicyano-1,4-benzoquinone
LAH=lithium aluminum hydride
TFA=trifluoroacetic acid
LDA=lithium diisopropylamide
THP=tetrahydropyranyl
NMM=N-methylmorpholine, 4-methylmorpholine
HMPA=hexamethylphosphoric triamide
DMPU=1,3-dimethypropylene urea
d=days
ppm=parts per million
kD=kiloDalton
LPS=lipopolysaccharide
PMA=phorbol myristate acetate
SPA=scintillation proximity assay
EDTA=ethylenediamine tetraacetic acid
FBS=fetal bovine serum
PBS=phosphate buffered saline solution
BrdU=bromodeoxyuridine
BSA=bovine serum albumin
FCS=fetal calf serum
DMEM=Dulbecco's modified Eagle's medium
pfu=plaque forming units
MOI=multiplicity of infection Reagents are commercially available or are prepared according to procedures in the literature. The physical data given for the compounds exemplified is consistent with the assigned structure of those compounds. $^1$H NMR spectra were obtained on VARIAN Unity Plus NMR spectrophotometers at 300 or 400 Mhz. Mass spectra were obtained on Micromass Platform II mass spectrometers from Micromass Ltd. Altrincham, UK, using either Atmospheric Chemical Ionization (APCI) or Electrospray Ionization (ESI). Analytical thin layer chromatography (TLC) was used to verify the purity of some intermediates which could not be isolated or which were too unstable for full characterisation, and to follow the progress of reactions. Unless otherwise stated, this was done using silica gel (Merck Silica Gel 60 F254). Unless otherwise stated, column chromatography for the purification of some compounds, used Merck Silica gel 60 (230-400 mesh), and the stated solvent system under pressure.

General Procedures

Procedure A—Representative method for 1H-indol-2,3-dione (isatin) formation: preparation of 6-H-1-thia-3,6-diaza-as-indacen-7,8-dione To a 1-L flask was added a magnetic stir bar, 85 g of sodium sulfate, and 100 mL of water. The mixture was magnetically stirred until all the solids were dissolved. To the resultant aqueous solution was added a solution of 6-aminobenzothiazole (4.96 g, 33.0 mmol) in 50 mL of 1 N aqueous hydrochloric acid and 10 mL of ethanol. The mixture was stirred, and chloral (6.0 g, (36 mmol) was added. To the resultant solution was added a solution of hydroxylamine hydrochloride (7.50 g, 108 mmol) in 30 mL of water. The final mixture was heated with stirring to a gentle boil until all solids dissappeared, and heating was continued for an additional 15 min. The flask was removed from the heat, and the solution was poured onto 500 g of ice. The mixture was stirred as the product precipatated from solution. The precipitate was collected by suction filtration, washed thoroughly with water, filtered, and air dried to provide 6.9 g (94%) of N-benzothiazol-6-yl-2-hydroxy-imino-acetamide: $^1$H NMR (DMSO-d$_6$): δ12.2 (s, 1H), 10.4 (s, 1H), 9.2 (s, 1H), 8.5 (s, 1H), 7.9 (d, 1H), 7.7 (m, 1H), 7.7 (s, 1H); APCI-MS m/z 220 (M–H)$^-$. To a 1-L 3-neck round bottom flask was placed a magnetic stir bar and 100 ml of concentrated sulfuric acid. The flask was fitted with a thermometer to monitor the temperature of the reaction. The sulfuric acid was heated to 100° C., and 10.0 g (45.2 mmol) of N-benzothiazol-6-yl-2-hydroxyimino-acetamide was added slowly. The solution was heated for ~1 h, and the reaction mixture was poured into 750 g of ice and water. The residual reaction mixture in the reaction vessel was washed out with an additional 20 mL of cold water. The aqueous slurry was stirred for about 1 h and filtered. The solid was washed thoroughly with water, filtered, and air dried to yield 4.3 g (46%) of 6-H-1-thia-3,6-diaza-as-indacen-7,8-dione: $^1$H NMR (DMSO-d$_6$): 11.1 (s, 1H), 9.2 (s, 1H), 8.2 (d, 1H), 7.0 (d, 1H); APCI-MS m/z 203 (M–H)$^-$.

EXAMPLE 1

Preparation of {4-[(2Z)-2-(4-chloro-5-hydroxy-6-isopropyl-2-oxo-1,2-dihydro-3H-indol-3-ylidene)hydrazino]phenyl}-N-methylmethanesulfonamide

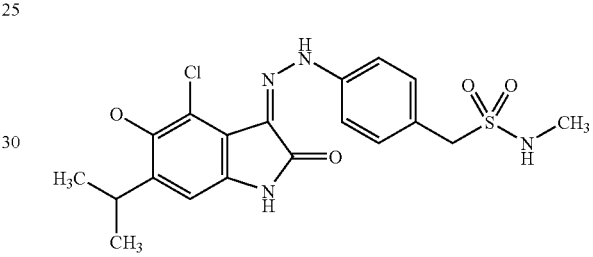

4-Chloro-5-hydroxy-6-I-propyl-1H-indole-2,3-dione was prepared from 3-chloro-4-hydroxy-5-I-propylaniline according to Procedure A. Condensation of 4-chloro-5-hydroxy-6-I-propyl-1H-indole-2,3-dione (1 equivalent) with 4-hydrazino-N-methyl-benzylsulfonamide (1.1 equivalent) was heated in EtOH to 80 C. for 1 h. Upon cooling H$_2$O was added and the solid was collected by vacuum filtration and dried in a vacuum oven at 60 C. to afford the title compound. Electrospray MS 436 (MH$^+$).

EXAMPLE 2

Preparation of N-(4-{[(Z)-(2-oxo-1,2-dihydro-3H-indol-3-ylidene)methyl]amino}phenyl)methanesulfonamide

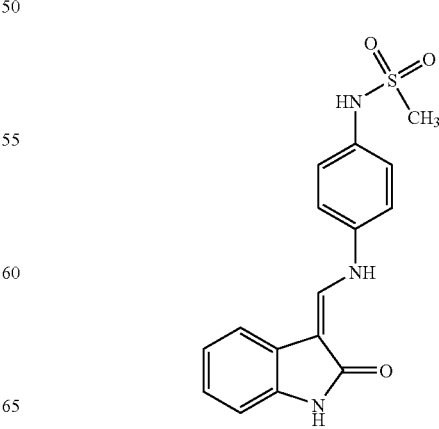

The title compound was prepared analogous to Example 5 from 3-(hydroxymethylene)-1,3-dihydro-2H-indol-2-one (0.164 g, 1.02 mmol) and N-(4-aminophenyl)-methanesulfonamide [53250-82-1, 0.186 g, 1.0 mmol] to provide a yellow solid (0.249 g). 1H NMR (DMSO) 10.67 (d, 1H); 10.45 (s, 1H); 9.56 (s, 1H); 8.50 (d, 1H); 7.52 (d, 1H); 7.35 (d, 2H); 7.18 (d, 2H); 6.95 (m, 1H); 6.89 (m, 1H); 6.80 (m, 1H); 2.92 (s, 3H), MP>250. APCI (–ve) 328. Analytical Calculated for $C_{16}H_{15}N_3O_3S$: C, 58.35; H, 4.59; N, 12.76; S, 9.73. Found: C, 58.40; H, 4.63; N, 12.75; S, 9.63.

EXAMPLE 3

Preparation of 4-{[(Z)-(2-oxo-1,2-dihydro-3H-indol-3-ylidene) methyl]amino}-N-(2-pyridinyl)benzenesulfonamide

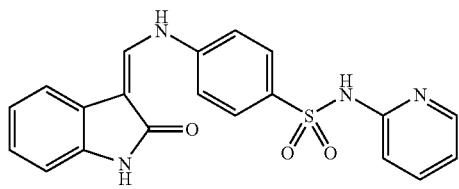

The title compound was prepared analogous to Example 5 from 3-(hydroxymethylene)-1,3-dihydro-2H-indol-2-one and sulfapyridine. Electrospray MS 393 (MH+).

EXAMPLE 4

Preparation of N-(5-methyl-1,3,4-thiadiazol-2-yl)-4-{[(Z)-(2-oxo-1,2-dihydro-3H-indol-3-ylidene)methyl]amino}benzenesulfonamide

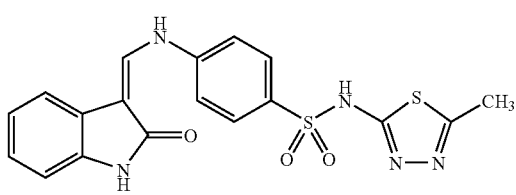

The title compound was prepared analogous to Example 5 from 3-(hydroxymethylene)-1,3-dihydro-2H-indol-2-one and 4-amino-N-(5-methyl[1,3,4]thiadiazol-2-yl)-benzenesulfonamide. $^1$H NMR (DMSO) 13.90 (bs, 1H); 10.84 (d, 1H); 10.58 (s, 1H); 8.62 (d, 1H); 7.81 (d, 2H); 7.60 (d, 1H); 7.55 (d, 2H); 7.12 (m, 1H); 6.95 (m, 1H); 7.84 (m, 1H); 2.48 (s, 3H). Electrospray MS 414 (MH+).

EXAMPLE 5

Preparation of 3-{[(Z)-(2-oxo-1,2-dihydro-3H-indol-3-ylidene) methyl]amino}benzenesulfonamide

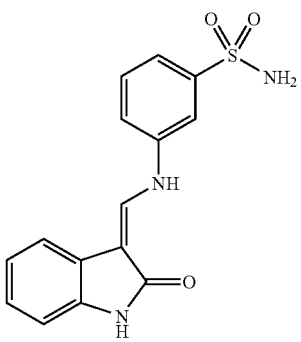

A mixture of 0.161 g (1.0 mmol) of (3Z)-3-(hydroxymethylene)-1,3-dihydro-2H-indol-2-one [1,2] and 0.180 g (1.05 mmol) of 3-aminobenzene-1-sulfonamide in 5 ml of EtOH was heated to 80° C. for 45 min. After cooling to ambient temperature, the solid was collected by vacuum filtration and air dried to afford 3-{[(Z)-(2-oxo-1,2-dihydro-3H-indol-3-ylidene)-methyl]amino}benzenesulfonamide as a yellow solid (0.25 g, 79%). mp>250° C.; $^1$H NMR (DMSO-$d_6$): 6.82 (d, J=7.7 Hz, 1H), 6.87-6.94 (m, 1H), 6.97-7.30 (m, 1H), 7.35 (s, 2H), 7.42-7.47 (m, 1H), 7.50-7.63 (m, 3H), 7.75 (t, J=1.8 Hz, 1H), 8.59 (d, J=12.1 Hz, 1H), 10.53 (s, 1H), 10.85 (d, J=12.3 Hz, 1H); APCI-MS: m/z 316 (m+H)+. Anal. Calcd for $C_{15}H_{13}N_3O_3S$: C, 57.13; H, 4.16; N, 13.32; S, 10.17. Found: C, 57.01; H, 4.23; N, 13.30; S, 10.11.

(1) Wolfbeis, Otto S.; Junek, Hans. Diacylenamines and -enoles, III. Formylation of CH2-acidic compounds via the anilinomethylene derivatives. Z. Naturforsch., B: Anorg. Chem., Org. Chem. (1979), 34B(2), 283-9 (2) Winn, Martin; Kyncl, John J. Aminomethylene oxindoles. U.S. (1979), 6 pp. U.S. Pat. No. 4,145,422

Note: One equivalent of strong acid, e.g., HCl or methanesulfonic acid, is generally required in this reaction. The acid can be supplied as the aniline salt or as a separate component. Similar conditions can be used for condensing anilines with 3-dimethylaminomethylene-, 3-t-butoxymethylene-, and 3-hydroxymethylene-substituted 2,3-dihydro-1H-indol-2-ones.

Biological Data

The compounds of the present invention have valuable pharmacologic properties. Different compounds from this class are particularly effective at inhibiting the trkA kinase enzyme at concentrations which range from 0.0001 to 1 μM and additionally show specificity relative to other kinases. Substrate phosphorylation assays were carried out as follows:

Screening format: Tyrosine kinase activity is being measured using a synthetic peptide substrate. The enzyme is a GST-fusion of the intracellular domain expressed in SF9 cells. The enzyme is expressed and purified by Regeneron. The enzyme is preincubated with cold ATP and Mg to allow autophosphorylation prior to running the screen. This increases the initial rate of catalysis approximately 3 fold. The assay is performed in 96 well microtitre plates, and reaction products are detected following filtration through millipore p81 phosphocellulose plates.

Assay Conditions

| | |
|---|---|
| Peptide substrate | Src peptide, NH2- RRRAAAEEIYGEI- NH2 |
| Peptide Km | 60 uM |
| ATP Km | 30 uM |
| Kcat/Km (peptide): | 1 × 10$^4$ |
| Assay conditions | 20-40 nM TrkA, 30 uM ATP, 50 uM Src peptide, 50 mM MOPS pH 7.5, 10 mM MgCl$^2$, 0.6 uCi $^{33}$P□ATP |
| Incubation | RT for 120' |
| Termination | Add 100 ul of 0.5% Phosphoric acid. Spot 100 ul onto millipore p81 96 well filter plate. Filter, wash 3× with 200 ul 0.5% phosphoric acid. Add 50 ul scintillation cocktail. Count in Packard Topcount |

Representative results are shown in Table 1 for the TrkA tyrosine kinase inhibition

TABLE 1

| Example | Substrate Phosphorylation TrkA |
|---|---|
| 1 | +++ |
| 2 | +++ |
| 3 | ++ |
| 4 | ++ |
| 5 | ++ |

| IC$_{50}$ values | Symbol |
|---|---|
| <0.010 uM | +++ |
| 0.010-0.10 uM | ++ |
| 0.10-1.0 uM | + |
| >1.0 uM | − |
| Not determined | ND |

Utility of Invention

Inhibitors of members of the TrK family of kinases find utility as agents in the treatment of a wide variety of disorders. These include cancers and pain.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein above may be applicable as a consequence of variations in the responsiveness of the mammal being treated for cancer conditions, or for other indications for the compounds of the invention as indicated above. Likewise, the specific pharmacologic responses observed may vary according to and depending upon the particular active compound selected or whether there are present certain pharmaceutical carriers, as well as the type of formulation and mode of administration employed, and such expected variations or differences in the results are contemplated in accordance with the objects and practices of the present invenion. It is intended, therefore, that the invention be limited only by the scope of the claims which follow and that such claims be interpreted as broadly as is reasonable.

We claim:

1. A method of inhibiting TrkA in a mammal, comprising administering a therapeutically effective amount of a compound of the formula I:

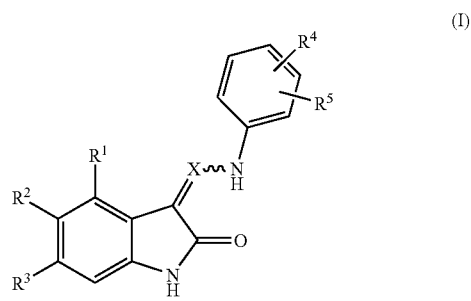

or salts, solvates, or physiological functional derivatives thereof
wherein:
  R$^1$ is hydrogen or halogen;
  R$^2$ is hydrogen, hydroxy or methoxy; or
  R$^3$ is hydrogen or C$_1$-C$_6$ branched alkyl;
  R$^4$ selected from the group consisting of 4'—CH$_2$—SO$_2$NHCH$_3$, 4'—NHSO$_2$CH$_3$,

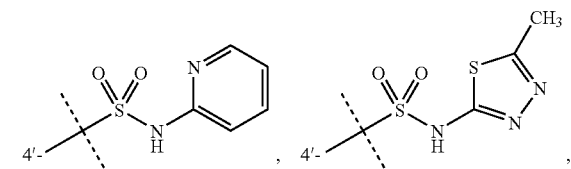

or 3'—SO$_2$NH$_2$;
  R$^5$ is hydrogen; and
  X is N or CH.

2. A method as claimed in claim 1, wherein R$^1$, is —Cl, R$^2$ is —OH, R$^3$ is isopropyl, R$^4$ is 4'—CH$_2$—SO$_2$NHCH$_3$, R$^5$ is —H and X is N.

3. A method as claimed in claim 1, wherein R$^1$, R$^2$, R$^3$, and R$^5$ are —H, R$^4$ is 4'—NHSO$_2$CH$_3$, and X is CH.

4. A method as claimed in claim 1, wherein R$^1$, R$^2$, R$^3$, and R$^5$ are —H, R$^4$ is

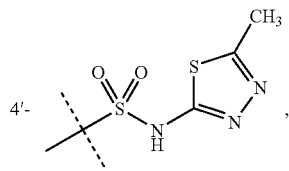

and X is CH.

5. A method as claimed in claim 1, wherein $R^1$, $R^2$, $R^3$, and $R^5$ are —H, $R^4$ is

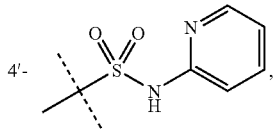

and X is CH.

6. A method as claimed in claim 1, wherein $R^1$, $R^2$, $R^3$, and $R^5$ are —H, $R^4$ is 3'—$SO_2NH_2$, and X is CH.

7. A method as claimed in claim 1, wherein X is CH.

8. A method as claimed in claim 1, wherein the compound of Formula I is selected from the group:

{4-[(2Z)-2-(4-chloro-5-hydroxy-6-isopropyl-2-oxo-1,2-dihydro-3H-indol-3-ylidene)hydrazino]phenyl}-N-methylmethanesulfonamide;

N-(4-{[(Z)-(2-oxo-1,2-dihydro-3H-indol-3-ylidene)methyl]amino}phenyl)methanesulfonamide;

4-{[(Z)-(2-oxo-1,2-dihydro-3H-indol-3-ylidene)methyl]amino}-N-(2-pyridinyl)benzenesulfonamide;

N-(5-methyl-1,3,4-thiadiazol-2-yl)-4-{[(Z)-(2-oxo-1,2-dihydro-3H-indol-3-ylidene)methyl]amino}bezenesulfonamide;

3-{[(Z)-(2-oxo-1,2-dihydro-3H-indol-3-ylidene)methyl]amino}benzenesulfonamide; and salts, solvates or physiologically functional derivatives thereof.

* * * * *